(12) United States Patent
Yaghmai (10) Patent No.: US 10,521,555 B2
(45) Date of Patent: Dec. 31, 2019

(54) VIDEO-ANALYSIS TAGGING OF HEALTHCARE SERVICES VIDEO RECORD

(71) Applicant: Elisha Yaghmai, Wichita, KS (US)

(72) Inventor: Elisha Yaghmai, Wichita, KS (US)

(73) Assignee: VIGILIAS LLC, Wichita, KS (US)

(*) Notice: Subject to any disclaimer, the term of this patent is extended or adjusted under 35 U.S.C. 154(b) by 0 days.

(21) Appl. No.: 15/625,768

(22) Filed: Jun. 16, 2017

(65) Prior Publication Data
US 2018/0268105 A1 Sep. 20, 2018

Related U.S. Application Data

(63) Continuation-in-part of application No. 15/460,813, filed on Mar. 16, 2017, now abandoned.

(51) Int. Cl.
| | |
|---|---|
| *G06F 19/00* | (2018.01) |
| *G06F 16/16* | (2019.01) |
| *G16H 40/20* | (2018.01) |
| *G16H 70/20* | (2018.01) |
| *G06F 16/71* | (2019.01) |
| *G16H 80/00* | (2018.01) |

(52) U.S. Cl.
CPC .......... *G06F 19/321* (2013.01); *G06F 16/164* (2019.01); *G16H 40/20* (2018.01); *G16H 70/20* (2018.01); *G06F 16/71* (2019.01); *G16H 80/00* (2018.01)

(58) Field of Classification Search
CPC .............. G06F 19/321; G06F 17/3012; G06F 17/30858; G11B 27/026; G11B 27/28
USPC ......................................................... 386/241
See application file for complete search history.

(56) References Cited

U.S. PATENT DOCUMENTS

| | | | | |
|---|---|---|---|---|
| 8,451,314 | B1 * | 5/2013 | Cline | .................. G06F 19/3418 348/14.05 |
| 9,179,192 | B1 * | 11/2015 | Ning | .................... G06F 16/7867 |
| 2002/0172498 | A1 * | 11/2002 | Esenyan | .............. G11B 27/034 386/241 |
| 2014/0366052 | A1 * | 12/2014 | Ives | .................. H04N 21/23418 725/19 |
| 2017/0243615 | A1 * | 8/2017 | Tabak | ................ G11B 27/3036 |
| 2018/0268104 | A1 | 9/2018 | Yaghmai | |

* cited by examiner

*Primary Examiner* — Loi H Tran (74) *Attorney, Agent, or Firm* — Schwabe Williamson & Wyatt, PC (57) ABSTRACT

Methods, systems, and storage media for generating an auto-tagged video record of a healthcare service are disclosed. In an embodiment, the auto-tagged video record of a healthcare service includes a digital video component and an audio component. One or more healthcare service tags may be generated by voice and/or video image recognition of the audio component and/or the digital video component to indicate one or more selected segments within healthcare service. The auto-tagged video record may be stored with the one or more healthcare service tags and, in embodiments, one or more of the selected segments may be accessed with respect to the healthcare service tags.

14 Claims, 7 Drawing Sheets

VIDEO-ANALYSIS TAGGING OF HEALTHCARE SERVICES VIDEO RECORD

CROSS REFERENCE TO RELATED APPLICATION

This application is a continuation-in-part of U.S. patent application Ser. No. 15/460,813, filed on Mar. 16, 2017, which is hereby incorporated by reference in its entirety.

FIELD

The present disclosure relates to the field of healthcare services, and in particular, to apparatuses, methods and storage media associated with providing a tagged video record of a healthcare service.

BACKGROUND

An aspect of providing healthcare services is preparing accurate records and notes, which may be extensive in some situations or practices. For some healthcare providers, the preparation of healthcare service records and notes may entail significant effort and time, which may reduce the time that the provider may otherwise devote to serving patients directly. In some practices, providers may prepare written or typed notes, either while providing healthcare services for a patient or afterwards. In other practices, providers may provide oral or spoken notes that may be transcribed by a human transcriptionist or a computer-based voice recognition system. These healthcare records or notes typically include just a summary of the healthcare services that are provided and/or observations or conclusions that may be reached in connection with providing the healthcare services.

BRIEF DESCRIPTION OF THE DRAWINGS

Embodiments will be readily understood by the following detailed description in conjunction with the accompanying drawings. To facilitate this description, like reference numerals designate like structural elements. Embodiments are illustrated by way of example, and not by way of limitation, in the figures of the accompanying drawings.

DETAILED DESCRIPTION

In the following detailed description, reference is made to the accompanying drawings which form a part hereof wherein like numerals designate like parts throughout, and in which is shown by way of illustrated embodiments that may be practiced. It is to be understood that other embodiments may be utilized and structural or logical changes may be made without departing from the scope of the present disclosure. Therefore, the following detailed description is not to be taken in a limiting sense, and the scope of embodiments is defined by the appended claims and their equivalents.

Various operations may be described as multiple discrete actions or operations in turn, in a manner that is most helpful in understanding the claimed subject matter. However, the order of description should not be construed to imply that the various operations are necessarily order-dependent. In particular, these operations might not be performed in the order of presentation. Operations described may be performed in a different order than the described embodiments. Various additional operations might be performed, or described operations might be omitted in additional embodiments.

The description may use the phrases "in an embodiment", "in an implementation", or in "embodiments" or "implementations", which may each refer to one or more of the same or different embodiments. Furthermore, the terms "comprising," "including," "having," and the like, as used with respect to embodiments of the present disclosure, are synonymous.

Also, it is noted that example embodiments may be described as a process depicted with a flowchart, a flow diagram, a data flow diagram, a structure diagram, or a block diagram. Although a flowchart may describe the operations as a sequential process, many of the operations may be performed in parallel, concurrently, or simultaneously. In addition, the order of the operations may be re-arranged. A process may be terminated when its operations are completed, but may also have additional steps not included in a figure. A process may correspond to a method, a function, a procedure, a subroutine, a subprogram, and the like. When a process corresponds to a function, its termination may correspond to a return of the function to the calling function a main function.

As disclosed herein, the term "memory" may represent one or more hardware devices for storing data, including random access memory (RAM), magnetic RAM, core memory, read only memory (ROM), magnetic disk storage mediums, optical storage mediums, flash memory devices or other machine readable mediums for storing data. The term "computer-readable medium" may include, but is not limited to, memory, portable or fixed storage devices, optical storage devices, and various other mediums capable of storing, containing or carrying instructions or data.

Furthermore, example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium. A code segment may represent a procedure, a function, a subprogram, a program, a routine, a subroutine, a module, program code, a software package, a class, or any combination of instructions, data structures, program statements, and the like.

As used herein, the term "network element", may be considered synonymous to or referred to as a networked computer, networking hardware, network equipment, router, switch, hub, bridge, gateway, or other like device. The term "network element" may describe a physical computing device of a network with wired or wireless communication links. Furthermore, the term "network element" may describe equipment that provides radio baseband functions for data or voice connectivity between a network and one or more users.

Figure 1:
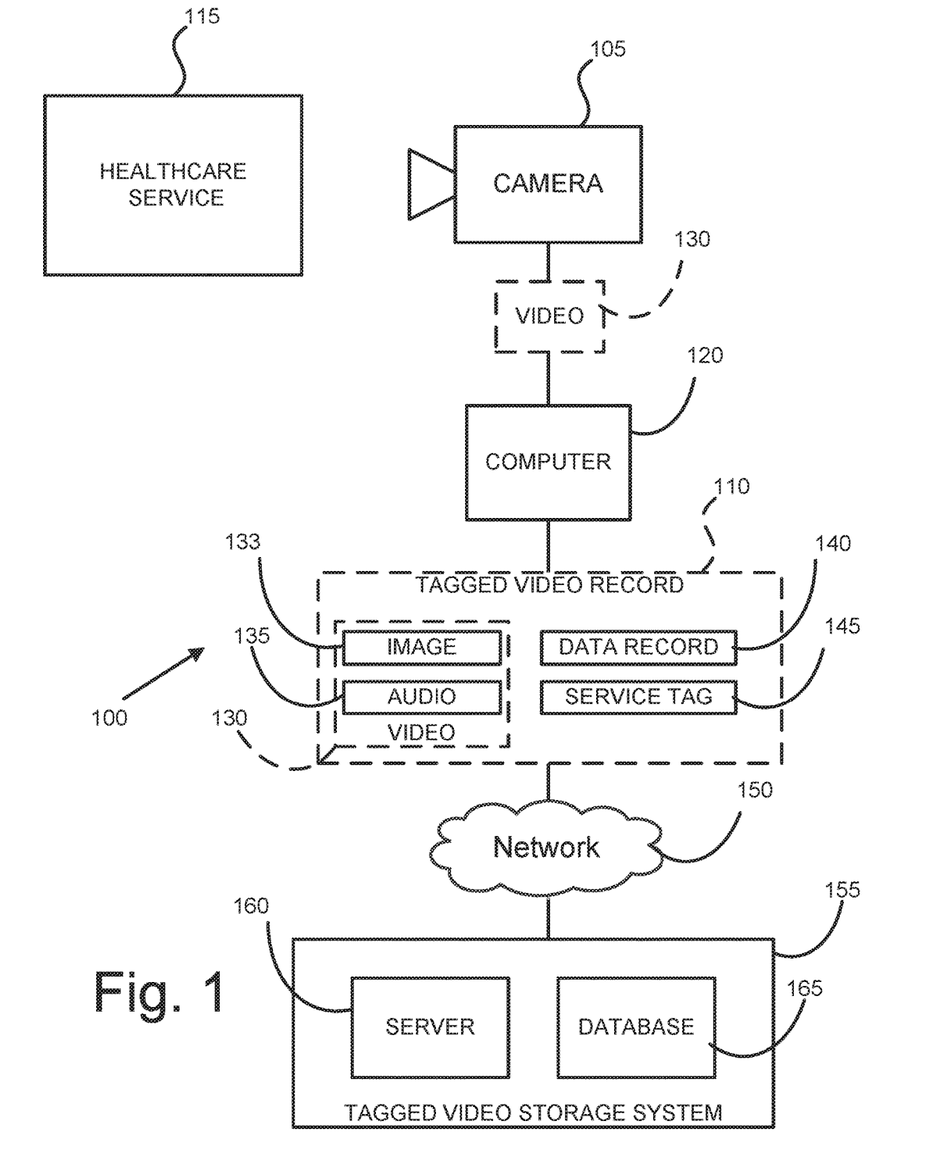
FIG. 1 illustrates a tagged video record system that may form a tagged digital video record of or relating to a healthcare service, according to some embodiments.

FIG. 1 illustrates a tagged video record system 100 that may include a digital video camera 105 that may be in communication with and/or under control of a computer 120 to form a tagged digital video record 110 of or relating to a healthcare service 115. In embodiments, the healthcare service 115 may include or relate to a medical service or procedure. In other embodiments, the healthcare service 115 may include or relate to another healthcare service, which may include or relate to healthcare fields that may be deemed other than medical, and may include dental services, psychological or counseling services, or any of various other types of healthcare services such as chiropractic, naturopathic, acupuncture-related, etc.

In one embodiment, video camera 105 may be positioned to form digital video record 130 of or relating to healthcare service 115 that may be provided to a patient by a healthcare provider, in-person, wherein the digital video record 130 may include the healthcare provider and/or the patient. In another embodiment, video camera 105 may be positioned to form digital video record 130 of or relating to healthcare service 115, which may include a consultation or other healthcare service, that may be provided to a patient by a healthcare provider remotely, such as over a digital network. In embodiments relating to healthcare series that may be provided remotely, a video camera 105 may be positioned to form digital video record 130 of or relating to the healthcare provider that provides the healthcare service 115, and another video camera 105 may be positioned to form a digital video record 130 of or relating to the patient that receives the healthcare service 115.

The tagged video record 110 may include one or more information or data components which may include any or all of digital video record 130, which may include a digital image component 133 of or relating to healthcare service 115 and an audio component 135, which may include a continuous audio record of or relating to healthcare service 115. In some embodiments, digital image component 133 may include continuous moving imagery as may be exemplified by conventional video. In other embodiments, digital image component 133 may additionally or alternatively include successive still images. Tagged video record 110 may include one or more healthcare data records 140, which may include patient healthcare data other than that of digital video 130 and may include patient healthcare data such as, for example, pulse rate, blood pressure, healthcare imagery, healthcare provider notations, etc., and/or one or more healthcare service tags 145, which may indicate one or more selected portions, times, or segments within healthcare service 115.

For example, one or more healthcare service tags 145 may indicate particular portions of the healthcare service 115, such as start and/or end times of selected examinations, procedures, and/or consultations. In embodiments, the one or more healthcare service tags 145 may be manually keyed or otherwise entered by the healthcare provider into computer 120 during healthcare service 115, or may be identified from tagged video record 110, such as by particular spoken words or other sounds initiated by the healthcare provider or by particular images in the tagged video record 110. In some embodiments, healthcare service tags 145, such as spoken words, may be identified within tagged video record 110 manually during subsequent review of tagged video record 110 by a transcriptionist, for example, or may be identified within tagged video record 110 by a voice recognition system.

The tagged video record 110 may be stored on computer 120 and/or another computer that may be local to or remote from video camera 105. As an example embodiment, the tagged video record 110 may be transmitted over a digital network 150, which may include a local private digital network and/or a public digital network such as the Internet, for storage at and subsequent retrieval from a tagged video storage system 155, which may include an application server 160 and/or a database 165. Tagged video record 110 may be subsequently accessed from tagged video storage system 155 in connection with a review of the record, such as by a healthcare provider, and one or more selected segments of the tagged video record 110 may be readily searched and/or accessed by selecting, referencing, or searching the corresponding healthcare service tags 145. As a result, tagged video record 110 may provide in combination a complete video record of healthcare service 115 and convenient ready access one or more tagged segments of healthcare service 115. Whenever tagged video record 110 is stored on computer 120 and/or another computer that may be local to video camera 105, computer 120 and/or another computer that may be local to video camera 105 may operate analogous to tagged video storage system 155.

Figure 2:
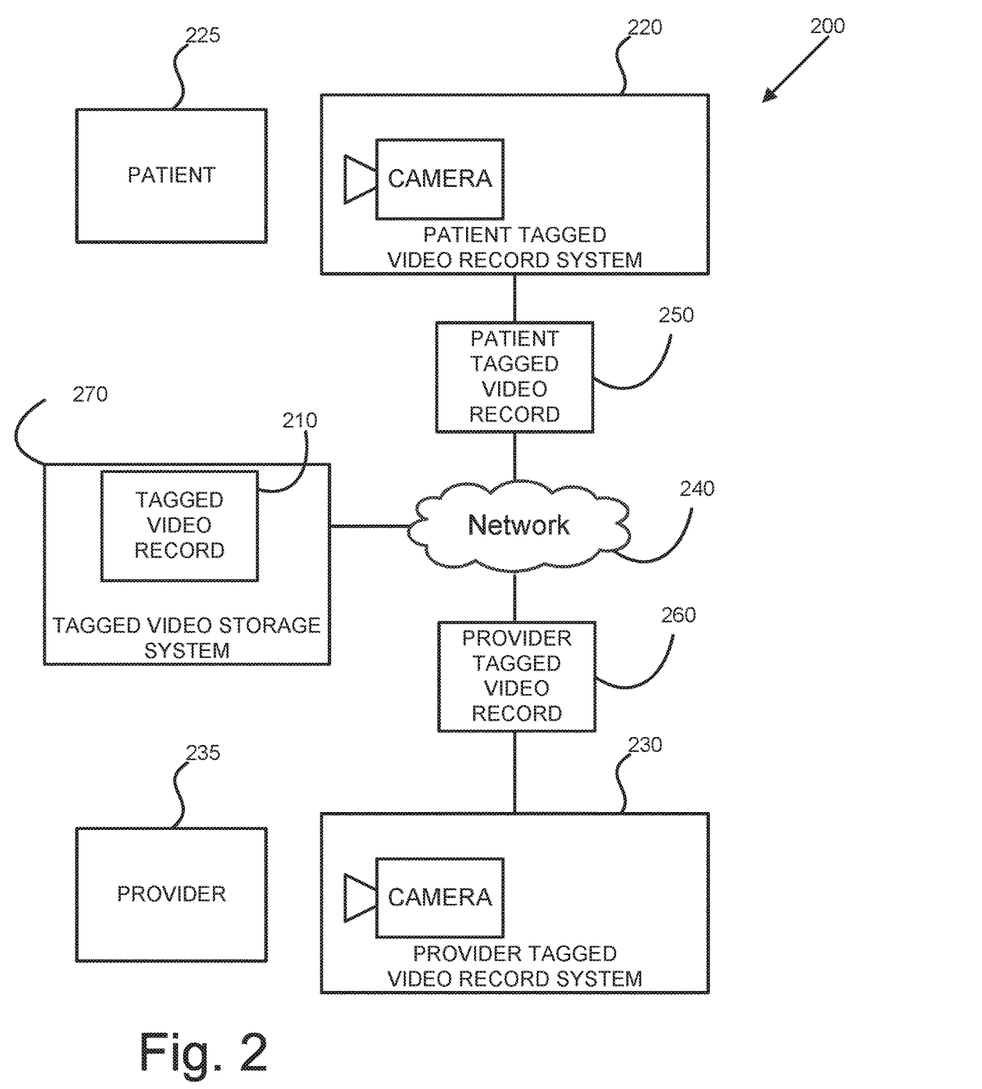
FIG. 2 is a block diagram illustrating operation of a remote-service tagged video record system, according to some embodiments.

FIG. 2 is a block diagram illustrating operation of a remote-service tagged video record system 200 that may include one or more tagged video record systems 100 (FIG. 1) in connection with providing a tagged video record 210 of a healthcare service that may be provided by a healthcare provider to a patient remotely via a computer network. For illustrative purposes, FIG. 2 will be described as being performed by patient tagged video record system 220 that may be local to and/or present with a patient 225, and a provider tagged video record system 230 that may be local to and/or present with the healthcare provider 235 at a location different from patient 225. Patient tagged video record system 220 and provider tagged video record system 230 may each be analogous to and or correspond with tagged video record system 100 (FIG. 1) or components of it. Patient tagged video record system 220 and provider tagged video record system 230 with may be in communication with each other over a digital network 240, which may include the Internet, for example.

In embodiments, patient tagged video record system 220 may generate a patient tagged video record 250, and provider tagged video record system 230 may generate a provider tagged video record 260. Patient tagged video record system 220 and provider tagged video record system 230 may be in communication with each other over digital network 240. Patient tagged video record system 220 may provide patient tagged video record 250 or portions of it to provider tagged video record system 230 and to a tagged video storage system 270, which may be analogous and operate similar to tagged video storage system 155 (FIG. 1). Provider tagged video record system 230 may provide provider tagged video record 260 or portions of it to patient tagged video record system 220 and to tagged video storage system 270. In some embodiments, patient tagged video record 250 may be stored with and/or synchronized or correlated with provider tagged video record 260 at tagged video storage system 270 to form tagged video record 210. In other embodiments, patient tagged video record 250 may include only a video record and no healthcare data records and/or healthcare service tags.

Figure 3:
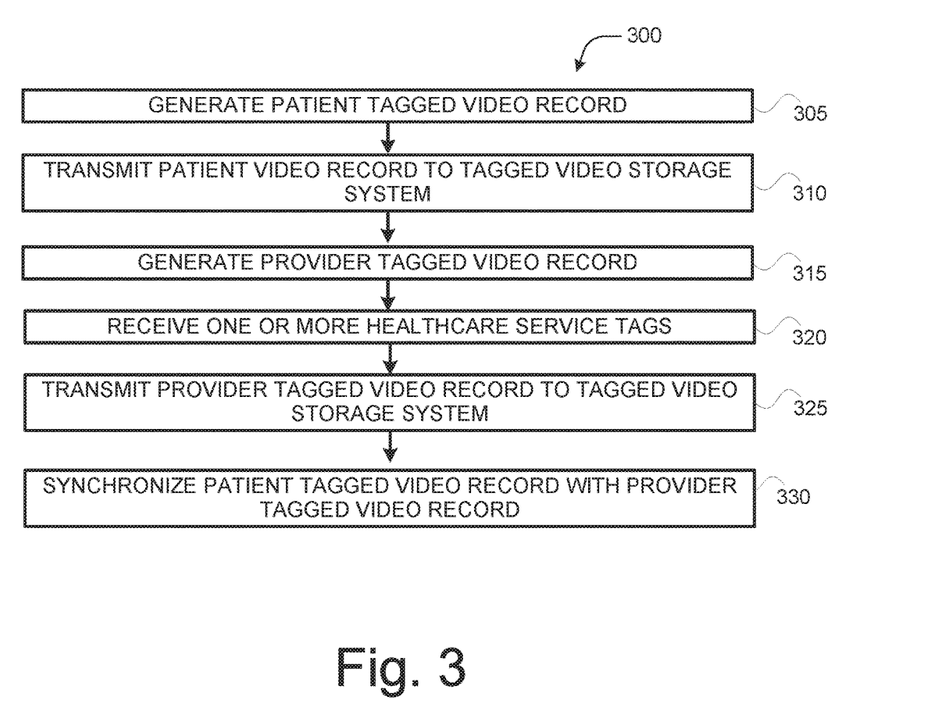
FIG. 3 is a flowchart illustrating an example process of a tagged video record method to provide a tagged video record of a healthcare service that may be provided by a healthcare provider to a patient remotely via a computer network, according to some embodiments.

FIG. 3 is a flowchart illustrating an example process 300 of a tagged video record method to provide a tagged video record of a healthcare service that may be provided by a healthcare provider to a patient remotely via a computer network. In some embodiments, the operations of process 300 may be described as being performed by patient tagged video record system 100 (FIG. 1) that may be local to and/or present with the patient, and a provider tagged video record system 100 that may be local to and/or present with the healthcare provider. The patient tagged video record system 100 and the provider tagged video record system 100 may be in communication with each other over a digital network which may include the Internet, for example. While particular examples and orders of operations are illustrated in FIG. 3, in various embodiments, these operations may be re-ordered, separated into additional operations, combined, or omitted altogether.

At operation 305, a patient tagged video record of a healthcare service may be generated by a patient tagged video record system. In embodiments, the patient tagged video record may include a digital video component, which may include a patient audio component, and may include one or more healthcare data records that may be provided by the patient.

At operation 310, the patient tagged video record may be transmitted by the patient tagged video record system to a tagged video storage system. In embodiments, the patient tagged video record may be transmitted to a tagged video storage system over a digital network that may include the Internet.

At operation 315, a provider tagged video record of a healthcare service may be generated by a provider tagged video record system. In embodiments, the provider tagged video record may include a digital video component, which may include a provider audio component, and may include one or more healthcare data records that may be provided or obtained by the provider.

At operation 320, one or more healthcare service tags that may indicate one or more selected portions, times, or segments within healthcare service, may be received from the healthcare provider. The healthcare service tags may be keyed by the healthcare provider into the provider tagged video record system and/or may be identified or correspond to particular words spoken by the healthcare provider. For example, the phrase "begin examination" may indicate the start of an examination portion of a healthcare service. In some embodiments, spoken healthcare service tags, as well as other comments, notes, observations, etc. spoken by the healthcare provider, may be identified and transcribed by a voice recognition system to the provider tagged video record, or may be later transcribed and indicated in the tagged video record by a human transcriptionist/operator.

At operation 325, the provider tagged video record may be transmitted by the provider tagged video record system to the tagged video storage system. In embodiments, the provider tagged video record may be transmitted to the tagged video storage system over a digital network that may include the Internet.

At operation 330, the patient tagged video record may be time-correlated or synchronized with the provider tagged video record by the tagged video storage system. As a result, healthcare service tags that may be applied to or in the provider tagged video record may be correlated with corresponding portions of the patient tagged video record.

In some embodiments, a video camera such as a video camera 105, which may operate in combination with a computer 120, may be local to and/or present with the patient and may be referred to as a patient video camera 105. In such embodiments, the patient video camera 105 may be used in substitution for patient tagged video record system 100 in process 300. In such embodiments, references in the description of process 300 to patient tagged video record may refer to a video record that may be generated by patient video camera 105.

Figure 4:
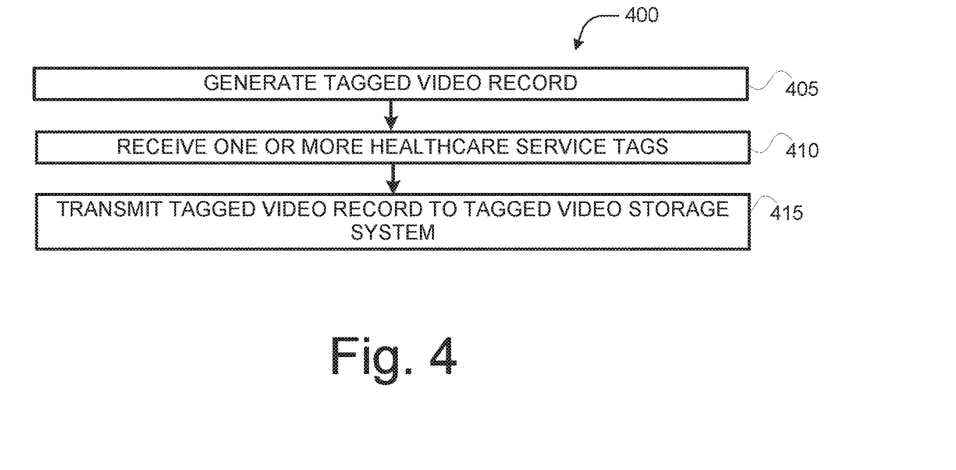
FIG. 4 is a flowchart illustrating an example process of a tagged video record method to provide a tagged video record of a healthcare service that may be provided by a healthcare provider to a patient in-person, according to some embodiments.

FIG. 4 is a flowchart illustrating an example process 400 of a tagged video record method to provide a tagged video record of a healthcare service that may be provided by a healthcare provider to a patient in-person. For illustrative purposes, the operations of process 400 will be described as being performed by tagged video record system 100 (FIG. 1) that may be local to and/or present with the patient and the healthcare provider. While particular examples and orders of operations are illustrated in FIG. 4, in various embodiments, these operations may be re-ordered, separated into additional operations, combined, or omitted altogether.

At operation 405, a tagged video record of a healthcare service may be generated by a tagged video record system. In embodiments, the tagged video record may include a digital video component, which may include an audio component, and may include one or more healthcare data records that may be provided or obtained by the provider.

At operation 410, one or more healthcare service tags that may indicate one or more selected portions, times, or segments within healthcare service, may be received from and/or entered by the healthcare provider.

At operation 415, the tagged video record may be transmitted by the tagged video record system to the tagged video storage system. In embodiments, the provider tagged video record may be transmitted to the tagged video storage system over a digital network that may include the Internet.

Figure 5:
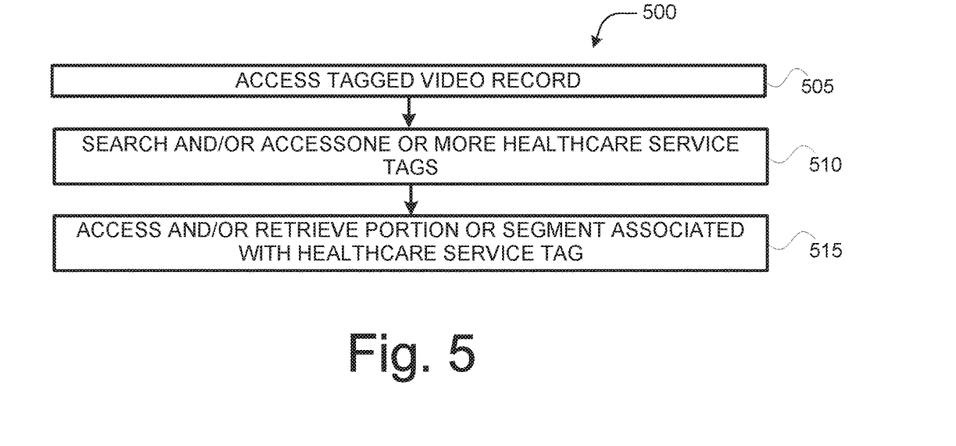
FIG. 5 is a flowchart illustrating an example process of a tagged video record access method to access a tagged video record of a healthcare service, according to some embodiments.

FIG. 5 is a flowchart illustrating an example process 500 of a tagged video record access method to access a tagged video record of a healthcare service. For illustrative purposes, the operations of process 500 will be described as being performed by a computer that may be in communication with or have access to the tagged video storage system where the tagged video record may be stored. The computer that may provide the operations of process 500 may be operated by or on behalf of a healthcare provider to access and/or retrieve the tagged video record of a healthcare service or one or more specified portions of it.

At operation 505, a tagged video record of a healthcare service may be accessed from a tagged video storage system. In embodiments, the tagged video record may include a digital video component, which may include an audio component, and may include one or more healthcare service tags that may indicate one or more selected portions, times, or segments within healthcare service. In embodiments, the tagged video record may include one or more healthcare data records that may be provided or obtained by the provider. In embodiments, the tagged video record may be accessed from the tagged video storage system over a digital network that may include the Internet.

At operation 510, one or more healthcare service tags may be searched and/or accessed within the tagged video record.

At operation 515, one or more selected portions, times, or segments and/or one or more healthcare data records that may be in the tagged video record in association with the one or more healthcare service tags that may accessed and/or retrieved.

Although certain embodiments have been illustrated and described herein for purposes of description, a wide variety of alternate and/or equivalent embodiments or implementations calculated to achieve the same purposes may be substituted for the embodiments shown and described without departing from the scope of the present disclosure. This application is intended to cover any adaptations or variations of the embodiments discussed herein, limited only by the claims.

Figure 6:
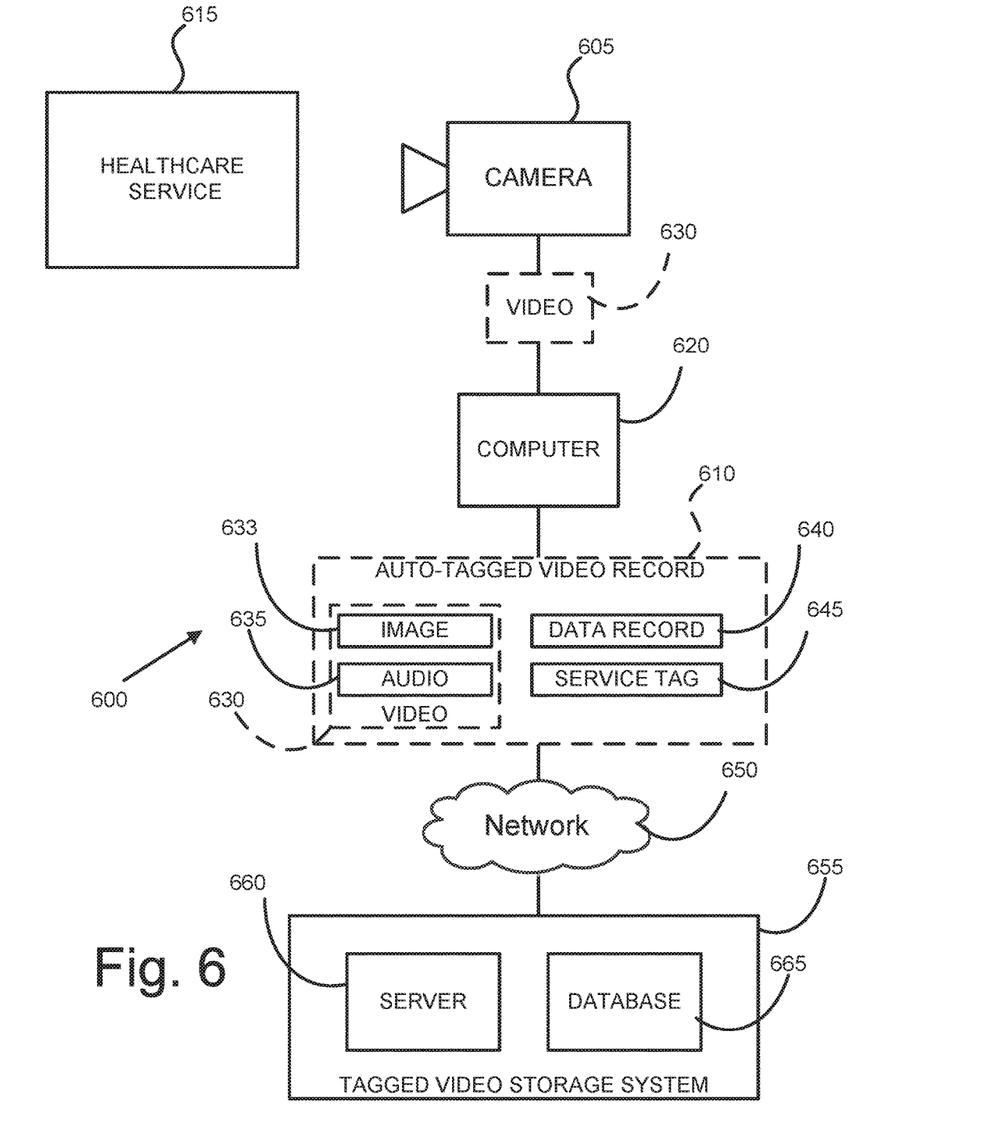
FIG. 6 illustrates a tagged video record system that may form a tagged digital video record of or relating to a healthcare service, according to some embodiments.

FIG. 6 illustrates an auto-tagged video record system 600 that may include a digital video camera 605 that may be in communication with and/or under control of a computer 620 to form an auto-tagged digital video record 610 of or relating to a healthcare service 615. In embodiments, the healthcare service 615 may include or relate to a medical service or procedure. In other embodiments, the healthcare service 615 may include or relate to another healthcare service, which may include or relate to healthcare fields that may be deemed other than medical, and may include dental services, psychological or counseling services, or any of various other types of healthcare services such as chiropractic, naturopathic, acupuncture-related, etc.

In one embodiment, video camera 605 may be positioned to form digital video record 630 of or relating to healthcare service 615 that may be provided to a patient by a healthcare provider, in-person, wherein the digital video record 630 may include the healthcare provider and/or the patient. In another embodiment, video camera 605 may be positioned to form digital video record 630 of or relating to healthcare service 615, which may include a consultation or other healthcare service, that may be provided to a patient by a healthcare provider remotely, such as over a digital network. In embodiments relating to healthcare series that may be provided remotely, a video camera 605 may be positioned to form digital video record 630 of or relating to the healthcare provider that provides the healthcare service 615, and another video camera 605 may be positioned to form a digital video record 630 of or relating to the patient that receives the healthcare service 615.

The auto-tagged video record 610 may include one or more information or data components which may include any or all of digital video record 630, which may include a digital image component 633 of or relating to healthcare service 615 and an audio component 635, which may include a continuous audio record of or relating to healthcare service 615. In some embodiments, digital image component 633 may include continuous moving imagery as may be exemplified by conventional video. In other embodiments, digital image component 633 may additionally or alternatively include successive still images. Auto-tagged video record 610 may include one or more healthcare data records 640, which may include patient healthcare data other than that of digital video 630 and may include patient healthcare data such as, for example, pulse rate, blood pressure, healthcare imagery, healthcare provider notations, etc., and/or one or more healthcare service tags 645, which may indicate one or more selected portions, times, or segments within healthcare service 615.

For example, one or more healthcare service tags 645 may indicate particular portions of the healthcare service 615, such as start and/or end times of selected examinations, procedures, and/or consultations. In embodiments, the one or more healthcare service tags 645 may be identified automatically from tagged video record 610, such as by particular spoken words or other sounds initiated by the healthcare provider or by particular images in the tagged video record 610, such as of a medical device and/or instrument (e.g., stethoscope, otoscope, suture kit, ultrasound transducer, electrocardiogram contacts, a needle driver, or casting materials, a central line kit, etc.) and/or touching of or a gesture toward a selected portion of a patient's body by the healthcare provider. For example, a provider positioning an otoscope near a patient's ear or nose may correspond to a healthcare service tag 645 indicating beginning of an examination of the patient's ear or nose. In some embodiments, healthcare service tags 645 may correspond to spoken words and/or images of medical devices, instruments and/or regions of a patient's body that may be touched or examined by a healthcare provider.

Healthcare service tags 645 may be identified within tagged video record 610 automatically by a voice recognition system and/or a video recognition system. In some embodiments, the video recognition system may employ machine learning, sometimes referred to as deep learning, deep structured learning, and/or hierarchical learning, to identify within video images particular healthcare instruments, devices, and/or gestures. Similarly, in some embodiments, completion of a healthcare service or procedure may be indicated, such as by a gesture or verbal statement, which may also be identified automatically by video and/or voice recognition.

The auto-tagged video record 610 may be stored on computer 620 and/or another computer that may be local to or remote from video camera 605. As an example embodiment, the auto-tagged video record 610 may be transmitted over a digital network 650, which may include a local private digital network and/or a public digital network such as the Internet, for storage at and subsequent retrieval from a tagged video storage system 655, which may include an application server 660 and/or a database 665. Auto-tagged video record 610 may be subsequently accessed from tagged video storage system 655 in connection with a review of the record, such as by a healthcare provider, and one or more selected segments of the auto-tagged video record 610 may be readily searched and/or accessed by selecting, referencing, or searching the corresponding healthcare service tags 645. As a result, auto-tagged video record 610 may provide in combination a complete video record of healthcare service 615 and convenient ready access one or more tagged segments of healthcare service 615. Whenever auto-tagged video record 610 is stored on computer 620 and/or another computer that may be local to video camera 605, computer 620 and/or another computer that may be local to video camera 605 may operate analogous to tagged video storage system 655.

Figure 7:
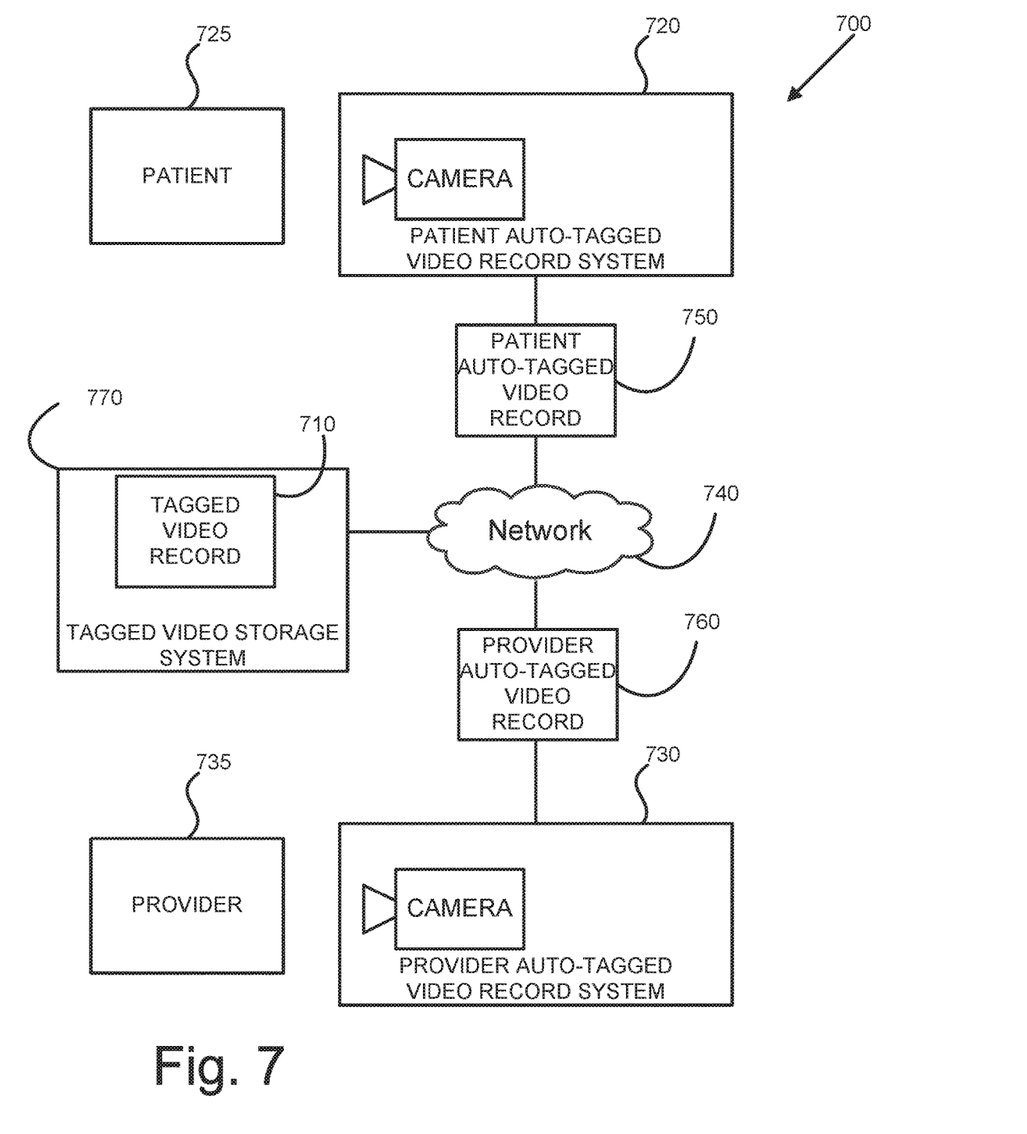
FIG. 7 is a block diagram illustrating operation of a remote-service tagged video record system, according to some embodiments.

FIG. 7 is a block diagram illustrating operation of a remote-service auto-tagged video record system 700 that may include one or more auto-tagged video record systems 600 (FIG. 6) in connection with providing an auto-tagged video record 710 of a healthcare service that may be provided by a healthcare provider to a patient remotely via a computer network. For illustrative purposes, FIG. 7 will be described as being performed by patient auto-tagged video record system 720 that may be local to and/or present with a patient 725, and a provider auto-tagged video record system 730 that may be local to and/or present with the healthcare provider 735 at a location different from patient 725. Patient auto-tagged video record system 720 and provider auto-tagged video record system 730 may each be analogous to and or correspond with auto-tagged video record system 600 (FIG. 6) or components of it. Patient auto-tagged video record system 720 and provider auto-tagged video record system 730 with may be in communication with each other over a digital network 740, which may include the Internet, for example.

In embodiments, patient auto-tagged video record system 720 may generate a patient auto-tagged video record 750, and provider auto-tagged video record system 730 may generate a provider auto-tagged video record 760. Patient auto-tagged video record system 720 and provider auto-tagged video record system 730 may be in communication with each other over digital network 740. Patient auto-tagged video record system 720 may provide patient auto-tagged video record 750 or portions of it to provider auto-tagged video record system 730 and to a tagged video storage system 770, which may be analogous and operate similar to tagged video storage system 655 (FIG. 6). Provider auto-tagged video record system 730 may provide provider auto-tagged video record 760 or portions of it to patient tagged video record system 720 and to tagged video storage system 770. In some embodiments, patient auto-tagged video record 750 may be stored with and/or synchronized or correlated with provider auto-tagged video record 760 at tagged video storage system 770 to form auto-tagged video record 710. In other embodiments, patient auto-tagged video record 750 may include only a video record and no healthcare data records and/or healthcare service tags.

Figure 8:
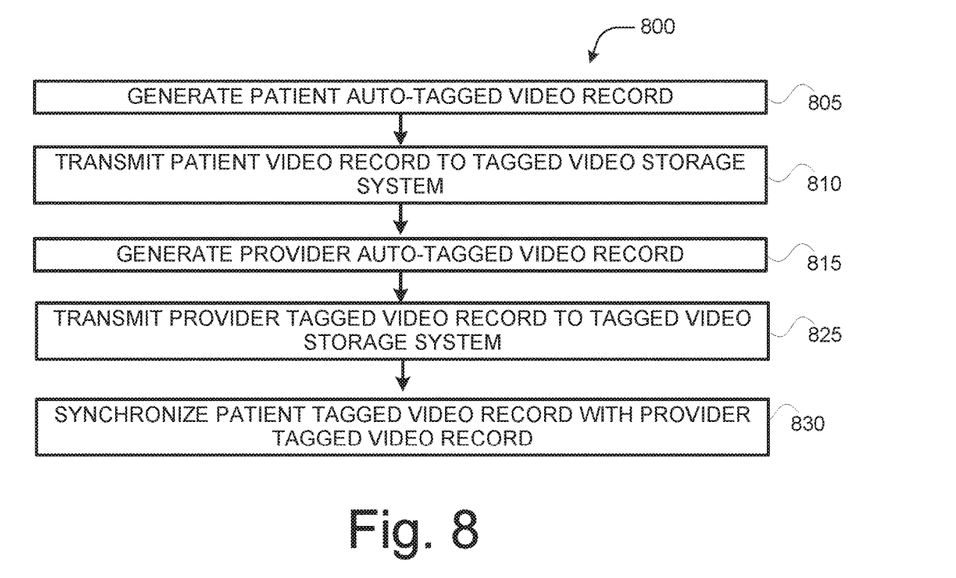
FIG. 8 is a flowchart illustrating an example process of a tagged video record method to provide a tagged video record of a healthcare service that may be provided by a healthcare provider to a patient remotely via a computer network, according to some embodiments.

FIG. 8 is a flowchart illustrating an example process 800 of an auto-tagged video record method to provide an auto-tagged video record of a healthcare service that may be provided by a healthcare provider to a patient remotely via a computer network. In some embodiments, the operations of process 800 may be described as being performed by patient auto-tagged video record system 600 (FIG. 6) that may be local to and/or present with the patient, and a provider auto-tagged video record system 600 that may be local to and/or present with the healthcare provider. The patient auto-tagged video record system 600 and the provider auto-tagged video record system 600 may be in communication with each other over a digital network which may include the Internet, for example. While particular examples and orders of operations are illustrated in FIG. 8, in various embodiments, these operations may be re-ordered, separated into additional operations, combined, or omitted altogether.

At operation 805, a patient auto-tagged video record of a healthcare service may be generated by a patient auto-tagged video record system. In embodiments, the patient auto-tagged video record may include a digital video component, which may include a patient audio component, and may include one or more healthcare data records that may be provided by the patient, wherein healthcare tags may be applied to the digital video component automatically by operation of video image and/or voice recognition operations.

At operation 810, the patient auto-tagged video record may be transmitted by the patient auto-tagged video record system to a tagged video storage system. In embodiments, the patient tagged video record may be transmitted to a tagged video storage system over a digital network that may include the Internet.

At operation 815, a provider auto-tagged video record of a healthcare service may be generated by a provider auto-tagged video record system. In embodiments, the provider tagged video record may include a digital video component, which may include a provider audio component, and may include one or more healthcare data records that may be applied to the digital video component automatically by operation of video image and/or voice recognition operations.

In embodiments, the healthcare service tags may be generated automatically by operation of voice and/or video image recognition and may be based on particular words spoken by the healthcare provider and/or devices, tools, equipment used by the provider and/or the patient. For example, the phrase "begin examination" may indicate the start of an examination portion of a healthcare service. In some embodiments, spoken healthcare service tags, as well as other comments, notes, observations, etc. spoken by the healthcare provider, may be identified and transcribed by a voice recognition system to the provider tagged video record, or may be later transcribed and indicated in the tagged video record by a human transcriptionist/operator.

At operation 825, the provider auto-tagged video record may be transmitted by the provider tagged video record system to the tagged video storage system. In embodiments, the provider auto-tagged video record may be transmitted to the tagged video storage system over a digital network that may include the Internet.

At operation 830, the patient auto-tagged video record may be time-correlated or synchronized with the provider tagged video record by the tagged video storage system. As a result, healthcare service tags that may be applied to or in the provider tagged video record may be correlated with corresponding portions of the patient tagged video record.

In some embodiments, a video camera such as a video camera 605, which may operate in combination with a computer 620, may be local to and/or present with the patient and may be referred to as a patient video camera 605. In such embodiments, the patient video camera 605 may be used in substitution for patient tagged video record system 600 in process 800. In such embodiments, references in the description of process 800 to patient tagged video record may refer to a video record that may be generated by patient video camera 605. In still other embodiments, untagged patient and provider video records may be transmitted to the tagged video storage system, where healthcare tags may be automatically identified in and incorporated to provide a patient auto-tagged video record and a provider auto-tagged video record.

Figure 9:
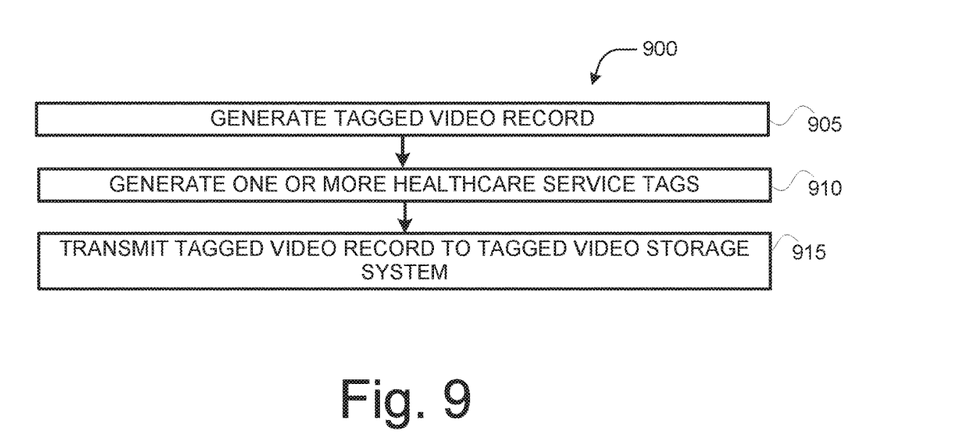
FIG. 9 is a flowchart illustrating an example process of a tagged video record method to provide a tagged video record of a healthcare service that may be provided by a healthcare provider to a patient in-person, according to some embodiments.

FIG. 9 is a flowchart illustrating an example process 900 of an auto-tagged video record method to provide a tagged video record of a healthcare service that may be provided by a healthcare provider to a patient in-person. For illustrative purposes, the operations of process 900 will be described as being performed by auto-tagged video record system 600 (FIG. 6) that may be local to and/or present with the patient and the healthcare provider. While particular examples and orders of operations are illustrated in FIG. 9, in various embodiments, these operations may be re-ordered, separated into additional operations, combined, or omitted altogether.

At operation 905, a tagged video record of a healthcare service may be generated by an tagged video record system. In embodiments, the tagged video record may include a digital video component, which may include an audio component, and may include one or more healthcare data records that may be provided or obtained by the provider.

At operation 910, one or more healthcare service tags that may indicate one or more selected portions, times, or segments within healthcare service to form an auto-tagged video record. The auto-tagged video record may be generated automatically by operation of voice and/or video image recognition operations that may employ deep learning and/or machine learning, for example.

At operation 915, the auto-tagged video record may be transmitted by the auto-tagged video record system to the tagged video storage system. In embodiments, the provider auto-tagged video record may be transmitted to the tagged video storage system over a digital network that may include the Internet.

What is claimed:

1. A method, comprising:
    generating a video record of a healthcare service, wherein the video record of the healthcare service includes a digital image component and an audio component;
    generating automatically from the video record one or more healthcare service tags that indicate one or more selected segments within the healthcare service, wherein one or more of the healthcare service tags include a machine-recognized image of a healthcare provider positioning a healthcare device near a selected portion of a patient body during the healthcare service; and
    forming a tagged video record with the video record and the one or more healthcare service tags, wherein the tagged video record includes a healthcare provider auto-tagged video record and a patient auto-tagged video record.

2. The method of claim 1, further comprising: transmitting the tagged video record over a digital network to store the tagged video record with the one or more healthcare service tags.

3. The method of claim 1, wherein the one or more healthcare service tags are associated with the provider auto-tagged video record.

4. The method of claim 1, further comprising: synchronizing the provider auto-tagged video record and the patient auto-tagged video record.

5. The method of claim 1, further comprising: accessing a selected segment of the tagged video record with respect to a corresponding one of the healthcare service tags.

6. The method of claim 1, wherein the tagged video record relates to a healthcare service provided remotely over a digital network.

7. The method of claim 1, wherein one or more of the healthcare service tags include a spoken statement from the healthcare provider made during the healthcare service.

8. At least one non-transitory computer-readable medium comprising instructions, wherein execution of the instructions by a computing device is to cause the computing device to:
    generate a video record of a healthcare service, wherein the video record of the healthcare service includes a digital image component and an audio component;
    generate by machine recognition one or more healthcare service tags that indicate one or more selected segments within the healthcare service, wherein one or more of the healthcare service tags include a machine-recognized image of a healthcare provider positioning a healthcare device near a selected portion of a patient body during the healthcare service; and
    form an auto-tagged video record with the video record and the one or more healthcare service tags, wherein the auto-tagged video record includes a provider auto-tagged video record and a patient auto-tagged video record.

9. The computer-readable medium of claim 8, wherein execution of the instructions is to cause the computing device to transmit the auto-tagged video record over a network to be stored.

10. The computer-readable medium of claim 8, wherein the patient auto-tagged video record is separate from the provider tagged video record.

11. The computer-readable medium of claim 10, wherein execution of the instructions is to cause the computing device to synchronize the provider auto-tagged video record and the patient auto-tagged video record.

12. The computer-readable medium of claim 8, wherein execution of the instructions is to cause the computing device to access a selected segment of the auto-tagged video record with respect to a corresponding one of the healthcare service tags.

13. The computer-readable medium of claim 8, wherein the auto-tagged video record relates to a healthcare service provided remotely over a digital network.

14. The computer-readable medium of claim 8, wherein one or more of the healthcare service tags include a spoken statement from the healthcare provider made during the healthcare service.

* * * * *